United States Patent [19]

Lesher et al.

[11] 4,431,651

[45] Feb. 14, 1984

[54] 2-PYRIDINONES AND THEIR USE AS CARDIOTONIC AGENTS

[75] Inventors: George Y. Lesher, Schodack; Baldev Singh, East Greenbush; Philip M. Carabateas, Schodack, all of N.Y.

[73] Assignee: Sterling Drug Inc., New York, N.Y.

[21] Appl. No.: 442,623

[22] Filed: Nov. 18, 1982

[51] Int. Cl.³ .................... A61K 31/44; C07D 213/56
[52] U.S. Cl. .................................. 424/263; 546/257; 546/301
[58] Field of Search ................. 546/257, 301; 424/263

[56] References Cited

U.S. PATENT DOCUMENTS

| | | | |
|---|---|---|---|
| 3,718,743 | 2/1973 | Shen et al. | 546/257 |
| 4,004,012 | 1/1977 | Lesher et al. | 546/257 |
| 4,072,746 | 2/1978 | Lesher et al. | 546/257 |
| 4,312,875 | 1/1982 | Lesher et al. | 546/257 |

*Primary Examiner*—Robert T. Bond
*Attorney, Agent, or Firm*—Robert K. Bair; B. Woodrow Wyatt; Paul E. Dupont

[57] ABSTRACT

3,4-Dihydro-3-$R_1$-4-$R_2$-5-Q-6-R-2(1H)-pyridinones (I), where $R_1$ and $R_2$ are each hydrogen or methyl, R is lower-alkyl, and Q is 4(or 3)-hydroxyphenyl, 4(or 3)-methoxyphenyl, 4(or 3)-pyridinyl or 4(or 3)-pyridinyl having one or two lower-alkyl substituents, or acid-addition salts thereof, and their preparation are shown. Also shown is the cardiotonic use of I where Q is 4(or 3)-hydroxyphenyl, 4(or 3)-pyridinyl or 4(or 3)-pyridinyl having one or two lower-alkyl substituents.

17 Claims, No Drawings

2-PYRIDINONES AND THEIR USE AS CARDIOTONIC AGENTS

BACKGROUND OF THE INVENTION (a) Field of the Invention

This invention relates to selected 3,4-dihydro-5-(pyridinyl or phenyl)-2(1H)-pyridinones, their use as cardiotonics, their preparation and intermediates therefor.

(b) Description of the Prior Art

Shen et al [U.S. Pat. No. 3,718,743, issued Feb. 27, 1973] show "5-phenyl-2-piperidinones and 5-phenyl-2-thiopiperidinones in compositions and methods for treating pain, fever and inflammation". The generic teaching of these piperidinones shows that "phenyl" can have one or two substituents at positions 2, 3, 4, 5 and/or 6, including alkyl, halogen, haloalkyl, aryl, nitro, amino, acylamino, acyl, carboxy, carbalkoxy, carbamyl, dialkylsulfamyl, alkylamino, dialkylamino, alkylmercapto, alkylsulfinyl and alkylsulfonyl. Various means of preparing the 5-phenyl-2-piperidinone final products are shown. In one procedure, a 2-chloro-5-phenylpyridine was heated with aqueous sodium hydroxide in dimethylformamide to produce the corresponding 5-phenyl-2(1H)-pyridinones which were then hydrogenated to produce the desired 5-phenyl-2-piperidinones. Among the intermediate 5-phenyl-2(1H)-pyridinones specifically shown is 5-(4-hydroxyphenyl)-2(1H)-pyridinone as well as its preparation by heating the corresponding 5-(4-methoxyphenyl)-2(1H)-pyridinone with pyridine hydrochloride under nitrogen.

Lesher and Opalka [U.S. Pat. Nos. 4,004,012, issued Jan. 18, 1977, and 4,072,746, issued Feb. 7, 1978] show inter alia, as cardiotonic agents 5-(pyridinyl)-2(1H)-pyridinones and their preparation by decarboxylating the corresponding 3-carboxy compounds. The disclosure of U.S. Pat. No. 4,072,746 also is shown in Lesher and Opalka U.S. Pat. Nos. 4,107,315, 4,137,233, 4,199,586 and 4,225,715.

Lesher, Opalka and Page [U.S. Pat. No. 4,312,875, issued Jan. 26, 1982] show, inter alia, as cardiotonic agents 5-(pyridinyl)-6-(lower-alkyl)-2(1H)-pyridinones and their preparation by decarboxylating the corresponding 3-carboxy compounds.

SUMMARY OF THE INVENTION

In a composition of matter aspect, the invention resides in 3,4-dihydro-3-$R_1$-4-$R_2$-5-Q-6-R-2(1H)-pyridinones (I), useful as cardiotonic agents, where Q, R, $R_1$ and $R_2$ are defined hereinbelow.

A composition aspect of the invention resides in a cardiotonic composition for increasing cardiac contractility in a patient, said composition comprising a pharmaceutically acceptable carrier and, as the active ingredient a cardiotonically effective amount of said 3,4-dihydro-3-$R_1$-4-$R_2$-5-Q-6-R-2(1H)-pyridinone (I).

A method aspect of the invention resides in the method for increasing cardiac contractility in a patient requiring such treatment which comprises administering a medicament comprising a pharmaceutically acceptable carrier and, as the active component, a cardiotonically effective amount of said 3,4-dihydro-3-$R_1$-4-$R_2$-5-Q-6-R-2(1H)-pyridinone (I).

A process aspect of the invention resides in the process which comprises reacting a 1-Q-2-alkanone of the formula Q—$CH_2$—C(=O)R (II) with an α-$R_1$-β-$R_2$-acrylonitrile of the formula $R_2$—CH=C($R_1$)CN (III) to produce 2-$R_1$-3-$R_2$-4-Q-4-(RCO)butanenitrile of the formula RC(=O)CH(Q)CH($R_2$)CH($R_1$)CN (IV), reacting IV with a strong acid to produce 3,4-dihydro-3-$R_1$-4-$R_2$-5-Q-6-R-2(1H)-pyridinone (I), where $R_1$ and $R_2$ are each hydrogen or methyl, R is lower-alkyl, and Q is 4(or 3)-pyridinyl, 4(or 3)-pyridinyl having one or two lower-alkyl substituents, or 4(or 3)-methoxyphenyl), and converting I where Q is 4(or 3)-methoxyphenyl to I where Q is 4(or 3)-hydroxyphenyl.

Another process aspect of the invention resides in the process which comprises reacting a 1-Q-2-alkanone (II) with a lower-alkyl α-$R_1$-β-$R_2$-acrylate of the formula $R_2$-CH=C($R_1$)COO$R_3$ (V) to produce lower alkyl 2-$R_1$-3-$R_2$-4-Q-4-(RCO)butanoate of the formula RC(=O)CH(Q)CH($R_2$)CH($R_1$)COO$R_3$ (VI), reacting VI with ammonia or source thereof to produce 3,4-dihydro-3-$R_1$-4-$R_2$-5-Q-6-R-2(1H)-pyridinone (I), where $R_1$, $R_2$, R and Q have the meanings given in the immediately preceding paragraph and $R_3$ is lower-alkyl, and converting I where Q is 4(or 3)-methoxyphenyl to I where Q is 4(or 3)-hydroxyphenyl.

Another aspect of the invention resides in the process which comprises reacting a 1-Q-2-alkanone (II) with an α-$R_1$-β-$R_2$-acrylamide of the formula $R_2$—CH=C($R_1$)—CONH$_2$ (VII) in an inert solvent in the presence of an alkali metal tertiary-butoxide to produce 3,4-dihydro-3-$R_1$-4-$R_2$-5-Q-6-R-2(1H)-pyridinone (I), where $R_1$, $R_2$, R and Q have the meanings given above and converting I where Q is 4(or 3)-methoxyphenyl to I where Q is 4(or 3)-hydroxyphenyl.

DETAILED DESCRIPTION INCLUSIVE OF PREFERRED EMBODIMENTS

A composition of matter aspect of the invention resides in a 3,4-dihydro-3-$R_1$-4-$R_2$-5-Q-6-R-2(1H)-pyridinone having the formula I

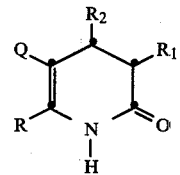

where Q is 4(or 3)-hydroxyphenyl, 4(or 3)-methoxyphenyl, 4(or 3)-pyridinyl or 4(or 3)-pyridinyl having one or two lower-alkyl substituents, $R_1$ and $R_2$ are each hydrogen or methyl and R is lower-alkyl, or an acid-addition salt thereof when Q is a pyridinyl substituent. The compounds of formula I where Q is 4(or 3)-hydroxyphenyl, 4(or 3)-pyridinyl or 4(or 3)-pyridinyl having one or two lower-alkyl substituents are useful as cardiotonics, as determined by standard pharmacological evaluation procedures. The compounds of formula I where Q is 4(or 3)-methoxyphenyl are useful as intermediates for preparing the cardiotonics of formula I where Q is 4(or 3)-hydroxyphenyl. Preferred embodiments are those of formula I where Q is 4(or 3)-pyridinyl, R is methyl or ethyl, and at least one of $R_1$ or $R_2$ is methyl.

A composition aspect of the invention resides in a cardiotonic composition for increasing cardiac contractility, said composition comprising a pharmaceutically acceptable carrier and, as the active component thereof, a cardiotonically effective amount of the compound of formula I where R, $R_1$ and $R_2$ are defined as in formula I and Q is 4(or 3)-hydroxyphenyl, 4(or 3)-pyridinyl or 4(or 3)-pyridinyl having one or two lower alkyl substituents, or pharmaceutically acceptable acid-addition salt thereof when Q is a pyridinyl substituent. Preferred embodiments of this composition aspect of the invention are those where the active component is the compound of formula I where Q is 4(or 3)-pyridinyl, R is methyl or ethyl, and at least one of $R_1$ or $R_2$ is methyl.

A method aspect of the invention resides in the method for increasing cardiac contractility in a patient requiring such treatment which comprises administering orally or parenterally in a solid or liquid dosage form to such patient a composition comprising a pharmaceutically acceptable carrier and, as active component thereof, a cardiotonically effective amount of the compound of formula I where R, $R_1$ and $R_2$ are defined as in formula I and Q is 4(or 3)-hydroxyphenyl, 4(or 3)-pyridinyl or 4(or 3)-pyridinyl having one or two lower-alkyl substituents, or pharmaceutically acceptable salt thereof when Q is a pyridinyl substituent. Preferred embodiments of this method aspect of the invention are those where the active component is the same as the active component of the preferred composition embodiments described in the immediately preceding paragraph.

A process aspect of the invention resides in the process for preparing the compound of formula I which comprises reacting a 1-Q-2-alkanone of the formula Q—$CH_2$—C(=O)R (II) with an $\alpha$-$R_1$-$\beta$-$R_2$-acrylonitrile of the formula $R_2$—CH=C($R_1$)CN (III) in the presence of a strong base to produce 2-$R_1$-3-$R_2$-4-Q-4-(RCO)butanenitrile having formula IV

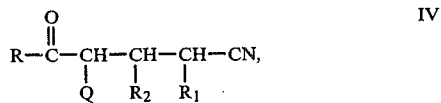

reacting IV with a strong acid to produce 3,4-dihydro-3-$R_1$-4-$R_2$-5-Q-6-R-2(1H)-pyridinone having formula I above, where $R_1$ and $R_2$ are each hydrogen or methyl, R is lower-alkyl, and Q is 4(or 3)-methoxyphenyl, 4(or 3)-pyridinyl or 4(or 3)-pyridinyl having one or two lower-alkyl substituents and converting the compound having formula I where Q is 4(or 3)-methoxyphenyl to the corresponding compound having formula I where Q is 4(or 3)-hydroxyphenyl. Preferred embodiments of this process aspect are those where the strong base in the first step is an alkali hydride or methoxide, the strong acid in the second step is a strong mineral acid and the products produced are those where Q is 4(or 3)-pyridinyl, R is methyl or ethyl and at least one of $R_1$ or $R_2$ is methyl.

Another process aspect of the invention resides in the process for preparing the compound of formula I which comprises reacting a 1-Q-2-alkanone (II supra) with a lower-alkyl $\alpha$-$R_1$-$\beta$-$R_2$-acrylate of the formula $R_2$—CH=C($R_1$)COO$R_3$ (V) to produce lower alkyl 2-$R_1$-3-$R_2$-4-Q-4-(RCO)butanoate having the formula VI

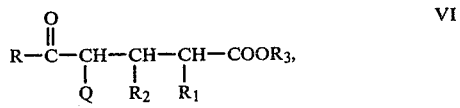

reacting VI with ammonia or source thereof to produce 3,4-dihydro-3-$R_1$-4-$R_2$-5-Q-6-R-2(1H)-pyridinone having formula I above, where $R_1$ and $R_2$ are each hydrogen or methyl, R and $R_3$ are each lower-alkyl, and Q is 4(or 3)-methoxyphenyl, 4(or 3)-pyridinyl or 4(or 3)-pyridinyl having one or two lower-alkyl substituents, and converting the compound having formula I where Q is 4(or 3)-methoxyphenyl to the compound having formula I where Q is 4(or 3)-hydroxyphenyl. Preferred embodiments of this process aspect are those where $R_3$ in the first step is methyl or ethyl, ammonium acetate is used as the source of ammonia in the second step and the products produced are those where Q is 4(or 3)-pyridinyl, R is methyl or ethyl and at least one of $R_1$ or $R_2$ is methyl.

Another aspect of the invention resides in the process for preparing the compound of formula I which comprises reacting a 1-Q-2-alkanone (II) with an $\alpha$-$R_1$-$\beta$-$R_2$-acrylamide of the formula $R_2$—CH=C($R_1$)CONH$_2$ (VII) in an inert solvent in the presence of a strong base, preferably an alkali metal tertiary-butoxide, to produce 3,4-dihydro-3-$R_1$-4-$R_2$-5-Q-6-R-2(1H)-pyridinone having formula I, where $R_1$ and $R_2$ are each hydrogen or methyl, R is lower-alkyl, and Q is 4(or 3)-methoxyphenyl, 4(or 3)-pyridinyl or 4(or 3)-pyridinyl having one or two lower-alkyl substituents, and converting the compound having formula I where Q is 4(or 3)-methoxyphenyl to the compound having formula I where Q is 4(or 3)-hydroxyphenyl. Preferred embodiments of this process aspect are those where dioxane and potassium or sodium tertiary-butoxide are used in the first step and the products produced are those where Q is 4(or 3)-pyridinyl, R is methyl or ethyl and at least one of $R_1$ or $R_2$ is methyl.

The term "lower-alkyl", as used herein to define R, $R_3$ or the substituents of (4 or 3)-pyridinyl, means alkyl radicals having from one to four carbon atoms which can be arranged as straight or branched chain, illustrated by methyl, ethyl, n-propyl, isopropyl, n-butyl, 2-butyl or isobutyl.

Illustrative of Q in formulas I, II, IV or VI where Q is 4- or 3-pyridinyl having one or two lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2,6-diethyl-4-pyridinyl, 2,6-diethyl-3-pyridinyl, 2,6-diisopropyl-4-pyridinyl, and the like.

The basic compounds of the invention having formula I where Q is a pyridinyl substituent are useful both in the free base and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base form of the cardiotonically active compounds of the invention are not vitiated by side effects ascribing to the anions. In practicing the invention, it is convenient to use the free base form; however, appropriate pharmaceutically acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compounds of formula I are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structure of the compounds of the invention were assigned on the basis of evidence provided by infrared, nuclear magnetic resonance and mass spectra, and by the correspondence of calculated and found values for the elemental analyses.

The manner of making and using the instant invention will now be generally described so as to enable a person skilled in the art of pharmaceutical chemistry to make and use the same.

The reaction of a 1-Q-2-alkanone of the formula Q—$CH_2$—C(=O)R (II) with an $\alpha$-$R_1$-$\beta$-$R_2$-acrylonitrile of the formula $R_2$—CH=C($R_1$)CN (III) to produce 2-$R_1$-3-$R_2$-4-Q-4-(RCO)butanenitrile (IV) is run by mixing the reactants at ambient temperature or in an ice bath in the presence of a strong base, such as an alkali hydride or alkaline metal hydride, preferably sodium hydride in mineral oil, or an alkali metal loweralkoxide, preferably sodium methoxide in a loweralkanol, preferably methanol. Other suitable strong bases include potassium tert.-butoxide, potassium methoxide, sodamide, benzyltrimethylammonium hydroxide, tetramethylammonium hydroxide, 1,5-diazobicyclo[4.3.0]non-5-ene (DBN), and the like. Other suitable solvents include p-dioxane, dimethylformamide, tetrahydrofuran, hexamethylphosphortriamide, N-methylpyrrolidone, ethanol, dimethyl sulfoxide, and the like.

The reaction of the 1-Q-2-alkanone (II) with a lower-alkyl $\alpha$-$R_1$-$\beta$-$R_2$-acrylate of the formula $R_2$—CH=C($R_1$)$COOR_3$ (V) to produce lower-alkyl 2-$R_1$-3-$R_2$-4-Q-4-(RCO)butanoate of formula VI is conveniently carried by mixing the reactants at about 0° C. to 100° C., preferably at about 20° C. to 40° C., in the presence or absence of a suitable solvent such as ethanol, methanol, dimethylformamide, dimethyl sulfoxide, nitromethane, and the like. Optionally, the reaction can be expedited by adding a small quantity of a substance such as a 40% solution of benzyltrimethylammonium hydroxide in methanol.

The conversion of 2-$R_1$-3-$R_2$-4-Q-4-(RCO)butanenitrile (IV) to 3,4-dihydro-3-$R_1$-4-$R_2$-5-Q-6-R-2(1H)-pyridinone (I) is carried out by reacting IV with a strong acid in the absence or presence of a suitable solvent. For example, the reaction can be run by adding a strong mineral acid such as concentrated sulphuric acid to IV cooled in an ice bath and then allowing the reaction mixture to stand at room temperature alternatively the reaction can be run by bubbling hydrogen chloride gas into a solution of IV in a suitable solvent such as absolute ethanol or other lower alkanol. Also, this conversion can be carried out using as the strong acid polyphosphoric acid or concentrated phosphoric acid, preferably heating on a steam bath.

The conversion of lower-alkyl 2-$R_1$-3-$R_2$-4-Q-4-(RCO)butanoate (VI) to 3,4-dihydro-3-$R_1$-4-$R_2$-5-Q-6-R-2(1H)-pyridinone (I) is conveniently carried out by heating VI with ammonia or a source of ammonia such as ammonium acetate in a suitable solvent such as ethanol. The reaction can be run at about 0° C. to 100° C., preferably about 50° C. to 90° C. Other sources of ammonia include ammonium chloride, ammonium carbonate, ammonium formate, and the like. Optionally, the reaction can be run under pressure using ammonia. Other suitable solvents include methanol, dimethylformamide, dimethyl sulfoxide, p-dioxane, nitromethane, and the like.

The reaction of 1-Q-2-alkanone (II) with an $\alpha$-$R_1$-$\beta$-$R_2$-acrylamide (VII) is conveniently run in an inert solvent and in the presence of a strong base, preferably an alkali metal tertiary-butoxide, preferably by mixing II, VII and potassium tertiary-butoxide in p-dioxane at ambient temperature and then heating if necessary up to about 100° C., to produce 3,4-dihydro-3-$R_1$-4-$R_2$-5-Q-6-R-2(1H)-pyridinone (I). Other suitable inert solvents and strong bases include those given above in the reaction of II and III to produce IV.

The conversion of 3,4-dihydro-3-$R_1$-4-$R_2$-5-Q-6-R-2(1H)-pyridinone (I) where Q is 4(or 3)-methoxyphenyl to the corresponding compound (I) where Q is 4(or 3)-hydroxyphenyl is conveniently carried out by conventional means of cleaving a methoxyphenyl compound to produce the corresponding hydroxyphenyl compound, such as by heating a collidine solution of the methoxyphenyl compound (I) in the presence of lithium iodide. This conversion can be run by refluxing I where Q is 4(or 3)-methoxyphenyl with concentrated (48%) hydrobromic acid, concentrated (57%) hydriodic acid, concentrated (85%) phosphoric acid or with aluminum trichloride or boron trifluoride in toluene.

The following examples will further illustrate the invention without, however, limiting it thereto.

A. 2-$R_1$-3-$R_2$-4-Q-4-(RCO)BUTANENITRILES

A-1. 4-Acetyl-4-(4-pyridinyl)butanenitrile

To a 13.5 g portion of 1-(4-pyridinyl)-2-propanone cooled in an ice bath was added 50 mg of sodium hydride as a 50% suspension in mineral oil and the resulting mixture was stirred for about 10 minutes. To the stirred solution was added 5.3 g of acrylonitrile dropwise over a period of 20 minutes. The ice bath was removed and the mixture was stirred at room temperature overnight. To the mixture was added 0.5 ml of acetic acid, the resulting mixture was partitioned between water and chloroform (150 ml of each) and the resulting mixture was shaken well. The two phases are separated and the chloroform phase was evaporated using a rotary evaporator to yield, as an oil, 17.5 g of material containing primarily 4-acetyl-4-(4-pyridinyl)butanenitrile, which was identified by its nmr spectrum and which was used in the next step without further purification.

A-2. 4-Acetyl-3-methyl-4-(4-pyridinyl)butanenitrile

To a stirred mixture mixture containing 59.6 g of 1-(4-pyridinyl)propanone and 100 ml of crotononitrile was added a solution of sodium methoxide in methanol obtained by adding 1 pellet of sodium shot to 20 ml of methanol. The reaction mixture was heated on a steam bath with stirring. After about 5 minutes, there was an exothermic reaction which raised the reaction temperature to 100° C. The resulting mixture was allowed to cool to room temperature and stand overnight (about 16 hours). To the reaction was added 100 ml of 10% acetic acid and 300 ml of methylene dichloride; and, the mixture was shaken well. The layers were separated and the methylene dichloride layer was dried over anhydrous magnesium sulfate and filtered. The methylene dichloride was distilled off in vacuo and the residual oil was distilled under vacuum using a small column to produce 85.0 g of 4-acetyl-3-methyl-4-(4-pyridinyl)butanenitrile, b.p. 130°–135° C. at 0.05 mm.

Following the procedure described in Example A-1 or A-2 using in place of 1-(4-pyridinyl)propanone and acrylonitrile or crotononitrile molar equivalent quantities of the appropriate 1-Q-2-alkanone and $\alpha$-R$_1$-$\beta$-R$_2$-acrylonitrile, it is contemplated that the corresponding 2-R$_1$-3-R$_2$-4-Q-4-(RCO)butanenitriles of Examples A-3 through A-12 can be obtained.

A-3. 4-Acetyl-2,3-dimethyl-4-(4-pyridinyl)butanenitrile, using 1-(4-pyridinyl)propanone and 2-methyl-2-butenenitrile.

A-4. 4-Acetyl-4-(3-pyridinyl)butanenitrile, using 1-(3-pyridinyl)propanone and acrylonitrile.

A-5. 4-Acetyl-2-methyl-4-(4-pyridinyl)butanenitrile, using 1-(4-pyridinyl)propanone and $\alpha$-methylacrylonitrile.

A-6. 1-Methyl-4-n-propanoyl-4-(4-pyridinyl)butanenitrile, using 1-(4-pyridinyl)butanone and $\alpha$-methylacrylonitrile.

A-7. 1-Methyl-4-(2-methylpropanoyl)-4-(4-pyridinyl)butanenitrile, using 1-(4-pyridinyl)-3-methyl-2-butanone and $\alpha$-methylacrylonitrile.

A-8. 2-Methyl-4-(n-pentanoyl)-4-(4-pyridinyl)butanenitrile, using 1-(4-pyridinyl)-2-hexanone and $\alpha$-methylacrylonitrile.

A-9. 4-Acetyl-2,3-dimethyl-4-(4-pyridinyl)butanenitrile, using 1-(2-methyl-4-pyridinyl)-2-propanone and 2-methyl-2-butenenitrile.

A-10. 2-Methyl-4-(2,6-dimethyl-4-pyridinyl)-4-n-propanoyl)butanenitrile, using 1-(2,6-dimethyl-4-pyridinyl)-2-butanone and $\alpha$-methylacrylonitrile.

A-11. 4-Acetyl-4-(4-methoxyphenyl)-2-methylbutanenitrile, using 1-(4-methoxyphenyl)-2-propanone and $\alpha$-methylacrylonitrile.

A-12. 2-Methyl-4-(3-methoxyphenyl)-4-n-propanoylbutanenitrile, using 1-(3-methoxyphenyl)-2-butanone and $\alpha$-methylacrylonitrile.

B. LOWER-ALKYL 2-R$_1$-3-R$_2$-4-Q-4-(RCO)BUTANOATES

B-1. Ethyl 4-Acetyl-3-methyl-4-(4-pyridinyl)butanoate

A mixture containing 13.5 g of 1-(4-pyridinyl)-2-propanone, 20 ml of ethyl crotonates and 0.5 ml of Triton B (a 40% solution of benzyltrimethylammonium hydroxide in methanol) was heated on a steam bath for 2 hours, allowed to cool to room temperature and to stand overnight. There was thus obtained as an oil a mixture containing as a major portion thereof ethyl 4-acetyl-3-methyl-4-(4-pyridinyl)butanoate, which was identified by its mass spectrum. This material was used in the next step without further purification.

Following the procedure described in Example B-1 but using in place of 1-(4-pyridinyl)-2-propanone and ethyl crotonate, molar equivalent quantities of the appropriate 1-Q-2-alkanone and lower-alkyl $\alpha$-R$_1$-$\beta$-R$_{2a}$-crylate, it is contemplated that the corresponding lower-alkyl 2-R$_1$-3-R$_2$-4-Q-4-(RCO)butanoates of Examples B-2 through B-12 can be obtained.

B-2. Ethyl 4-Acetyl-4-(4-pyridinyl)butanoate, using 1-(4-pyridinyl)-2-propanone and ethyl acrylate.

B-3. Methyl 4-Acetyl-2-methyl-4-(4-pyridinyl)butanoate, using 1-(4-pyridinyl)-2-propanone and methyl $\alpha$-methylacrylate.

B-4. Ethyl 4-Acetyl-2,3-dimethyl-4-(4-pyridinyl)butanoate, using 1-(4-pyridinyl)-2-propanone and ethyl $\alpha,\beta$-dimethylacrylate.

B-5. Ethyl 4-Acetyl-4-(3-pyridinyl)butanoate, using 1-(3-pyridinyl)-2-propanone and ethyl acrylate.

B-6. Ethyl 1-Methyl-4-n-propanoyl-4-(4-pyridinyl)butanoate, using 1-(4-pyridinyl)-2-butanone and ethyl $\alpha$-methylacrylate.

B-7. Ethyl 2-Methyl-4-(2-methyl-n-propanoyl)-4-(4-pyridinyl)butanoate, using 1-(4-pyridinyl)-3-methyl-2-butanone and ethyl $\alpha$-methylacrylate.

B-8. Ethyl 4-n-butanoyl-2-methyl-4-(4-pyridinyl)butanoate, using 1-(4-pyridinyl)-2-hexanone and ethyl $\alpha$-methylacrylate.

B-9. Ethyl 4-Acetyl-2,3-dimethyl-4-(2-methyl-4-pyridinyl)butanoate, using 1-(2-methyl-4-pyridinyl)-2-propanone and ethyl $\alpha,\beta$-dimethylacrylate.

B-10. Ethyl 2-Methyl-4-n-propanoyl-4-(2,6-dimethyl-4-pyridinyl)butanoate, using 1-(2,6-dimethyl-4-pyridinyl)-2-butanone and ethyl $\alpha$-methylacrylate.

B-11. Ethyl 4-Acetyl-4-(4-methoxyphenyl)-2-methyl butanoate, using 1-(4-methoxyphenyl)-2-propanone and ethyl $\alpha$-methylacrylate.

B-12. Ethyl 4-(3-Methoxyphenyl)-4-n-propanoyl-2-methyl butanoate, using 1-(3-methoxyphenyl)-2-butanone and ethyl $\alpha$-methylacrylate.

C. 3,4-DIHYDRO-3-R$_1$-4-R$_2$-5-Q-6-R-2(1H)-PYRIDINONES

C-1. 3,4-Dihydro-6-methyl-5-(4-pyridinyl)-2(1H)-pyridinone, alternatively named 4,5-dihydro-2-methyl-[3,4'-bipyridin]-6(1H)-one To a 17 g portion of 4-acetyl-4-(4-pyridinyl)butanenitrile cooled in an ice bath was added slowly 50 ml of concentrated sulphuric acid while the mixture was shaken slowly. The reaction mixture was allowed to stand in the ice bath for 2 hours and then at room temperature overnight; it was then poured onto ice (600 ml beaker half filled) and the resulting aqueous mixture was neutralized by adding aqueous ammonium hydroxide. The oily material that separated solidified while the mixture was allowed to stand at room temperature for 3 hours. The solid was collected, washed with water and dried to yield 13.2 g of material which was purified chromatographically using 500 g of silica gel and 15% of methanol in ether as the eluant. The least polar component was collected and recrystallized from isopropyl alcohol-ether to produce 6.3 g of 3,4-dihydro-6-methyl-5-(4-pyridinyl)-2(1H)-pyridinone, m.p. 175°–177° C.

Acid-addition salts of 3,4-dihydro-6-methyl-5-(4-pyridinyl)-2(1H)-pyridinone are conveniently prepared by adding to a mixture of 1 g of 3,4-dihydro-6-methyl-5-(4-pyridinyl)-2(1H)-pyridinone in about 20 ml of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 3,4-dihydro-6-methyl-5-(4-pyridinyl)-2(1H)-pyridinone and the appropriate acid, e.g., lactic acid or hydrochloric acid, to prepare respectively the lactate or hydrochloride salt of 3,4-dihydro-6-methyl-5-(4-pyridinyl)-2(1H)-pyridinone in aqueous solution.

C-2.

3,4-Dihydro-4,6-dimethyl-5-(4-pyridinyl)-2(1H)-pyridinone, alternatively named 4,5-dihydro-2,4-dimethyl-[3,4'-bipyridin]-6(1H)-one To a 2.0 g portion of 4-acetyl-3-methyl-4-(4-pyridinyl)butanenitrile dissolved in 20 ml of acetic acid was added dropwise 3 ml of sulfuric acid whereupon an exothermic reaction ensued. The reaction mixture was stirred for 4 hours, the acetic acid was evaporated off in vacuo and to the remaining material was added 10 ml of water followed by basification with 35% aqueous sodium hydroxide solution. The alkaline solution was extracted four times with ethyl acetate; the combined extracts were dried over anhydrous magnesium sulfate; the ethyl acetate was distilled off in vacuo; and, the remaining white solid was recrystallized from acetonitrile to produce 2.0 g of 3,4-dihydro-4,6-dimethyl-5-(4-pyridinyl)-2(1H)-pyridinone, m.p. 184°–186° C.

The same compound was prepared by the following procedure: Into a solution containing 81 g of 4-acetyl-3-methyl-4-(4-pyridinyl)butanenitrile dissolved in 250 ml of absolute ethanol was bubbled hydrogen chloride gas at ambient temperature with no cooling. After about 1 hour, a white solid began to crystallize. The reaction vessel was then stoppered and allowed to stand overnight at room temperature. The reaction mixture was evaporated to dryness in vacuo and the residue was dissolved in a small amount of water. The aqueous solution was made alkaline with concentrated ammonia hydroxide and the mixture was extracted with ethyl acetate. The ethyl acetate solution was dried over anhydrous magnesium sulfate, the mixture filtered and the filtrate evaporated in vacuo. The residue was slurried with acetonitrile and the solid, 5.4 g, was collected. This solid was combined with the product obtained as described in the immediately preceding paragraph along with the product obtained hereinbelow in Example C-3 and the combined material was recrystallized from about 250 ml of acetonitrile to yield 9.9 g of 3,4-dihydro-4,6-dimethyl-5-(4-pyridinyl)-2(1H)-pyridinone, m.p. 186°–188° C.

Acid-addition salts of 3,4-dihydro-4,6-dimethyl-5-(4-pyridinyl)-2(1H)-pyridinone are conveniently prepared by adding to a mixture of 1 g of 3,4-dihydro-4,6-dimethyl-5-(4-pyridinyl)-2(1H)-pyridinone in about 20 ml of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 3,4-dihydro-4,6-dimethyl-5-(4-pyridinyl)-2(1H)-pyridinone and the appropriate acid, e.g., lactic acid or hydrochloric acid, to prepare respectively the lactate or hydrochloride salt of 3,4-dihydro-4,6-dimethyl-5-(4-pyridinyl)-2(1H)-pyridinone in aqueous solution.

C-3.

3,4-Dihydro-4,6-dimethyl-5-(4-pyridinyl)-2(1H)-pyridinone

A mixture containing 24 g of ethyl 4-acetyl-3-methyl-4-(4-pyridinyl)butanoate, 7 g of ammonium acetate and 50 ml of ethanol was refluxed for 8 hours with stirring. The reaction mixture was then concentrated to dryness in vacuo and the remaining white solid was collected, washed with ethanol and dried to produce 1.8 g of 3,4-dihydro-4,6-dimethyl-5-(4-pyridinyl)-2(1H)-pyridinone, m.p. 184°–185° C. It's nmr and mass spectrum were consistent with the assigned structure.

C-4.

3,4-Dihydro-3,6-dimethyl-5-(4-pyridinyl)-2(1H)-pyridinone, alternatively named 4,5-dihydro-2,5-dimethyl[3,4'-bipyridin]-6(1H)-one A mixture containing 35 g of 1-(4-pyridinyl)-2-propanone, 25 g of α-methylacrylamide, 30 g of potassium-tert.-butoxide and 250 ml of p-dioxane was stirred at ambient temperature for 40 minutes during which time an exothermic reaction occurred. The reaction mixture was then heated on a steam bath for 90 minutes and stripped to dryness on a rotary evaporator. To the residue was added 200 ml of water and the aqueous mixture was acidified with acetic acid. The product was extracted with chloroform (two 300 ml portions) and the combined extracts stripped to dryness in vacuo. The gummy solid was dissolved in 200 ml of isopropyl alcohol, the hot solution treated with decolorizing charcoal and filtered, and the filtrate diluted with 300 ml of n-hexane. The crystalline precipitate was collected and dried in an oven at 80° C. to yield 25.4 g of 3,4-dihydro-3,6-dimethyl-5-(4-pyridinyl)-2(1H)-pyridinone, m.p. 148°–150° C. A second crop of 4.3 g, m.p. 147–150, was obtained from the mother liquor. The nmr spectrum of the product was consistent with the assigned structure.

Acid-addition salts of 3,4-dihydro-3,6-dimethyl-5-(4-pyridinyl)-2(1H)-pyridinone are conveniently prepared by adding to a mixture of 1 g of 3,4-dihydro-3,6-dimethyl-5-(4-pyridinyl)-2(1H)-pyridinone in about 20 ml of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 3,4-dihydro-3,6-dimethyl-5-(4-pyridinyl)-2(1H)-pyridinone and the appropriate acid, e.g., lactic acid or hydrochloric acid, to prepare respectively the lactate or hydrochloride salt of 3,4-dihydro-3,6-dimethyl-5-(4-pyridinyl)-2(1H)-pyridinone in aqueous solution.

C-5.
3,4-Dihydro-5-(4-methoxyphenyl)-6-methyl-2(1H)-pyridinone 13.9 g, m.p. 160°–162° C., was prepared following the procedure described in Example C-4 using 50 g of 1-(4-methoxyphenyl)-2-propanone, 28.4 g of acrylamide, 44.8 g of potassium tert.-butoxide, 400 ml of p-dioxane, stirring the reaction mixture at ambient temperature for 1 hour, heating the reaction mixture on a steam bath for 1 hour and then, after isolating the product as in the preceding example, crystallizing it once from isopropyl alcohol and once from 200 ml of ethanol.

C-6.
3,4-Dihydro-5-(4-hydroxyphenyl)-6-methyl-2(1H)-pyridinone

A mixture containing 9 g of 3,4-dihydro-5-(4-methoxyphenyl)-6-methyl-2(1H)-pyridinone, 100 ml of collidine and 38 g of lithium iodide was heated under reflux for 28 hours and then concentrated to dryness on a rotary evaporator. The residue was dissolved in 100 ml of water and again concentrated to dryness on a rotary evaporator; this process was repeated twice to remove the last traces of collidine. The solid residue was dissolved in water and the aqueous solution acidified with concentrated hydrochloric acid. The gummy solid that separated on chilling was collected, washed with water, dried at room temperature, recrystallized from ether-isopropyl alcohol using decolorizing charcoal and then chromatographed over 100 g of silica gel using 5% methanol in ether as eluant to produce 3.1 g of 3,4-dihydro-5-(4-hydroxyphenyl)-6-methyl-2(1H)-pyridinone, m.p. 197°–200° C.

C-7.
3,4-Dihydro-5-(4-methoxyphenyl)-3,6-dimethyl-2(1H)-pyridinone 42.2 g, m.p. 135–136, was prepared following the procedure described in Example C-5 using 50 g of 1-(4-methoxyphenyl)-2-propanone, 34 g of α-methyl acrylamide, 44.8 g of potassium tert.-butoxide, 300 ml of p-dioxane and recrystallization from isopropyl alcohol-n-hexane.

C-8.
3,4-Dihydro-5-(4-hydroxyphenyl)-3,6-dimethyl-2(1H)-pyridinone 6.6 g, m.p. 168°–170° C., was prepared following the procedure described in Example C-6 using 23.1 g of 3,4-dihydro-5-(4-methoxyphenyl)-3,6-dimethyl-2(1H)-pyridinone, 200 ml of collidine, 75 g of lithium iodide and recrystallization from 250 ml of boiling ethanol using decolorizing charcoal.

Following the procedure described in Example C-1 using in place of 4-acetyl-4-(4-pyridinyl)butanenitrile a corresponding molar equivalent quantity of 2-$R_1$-3-$R_2$-4-Q-4-(RCO)butanenitrile or following the procedure described in Example C-3 using in place of ethyl 4-acetyl-3-methyl-4-(4-pyridinyl)butanoate a molar equivalent quantity of the appropriate lower-alkyl 2-$R_1$-3-$R_2$-4-Q-4-(RCO)butanoate it is contemplated that the corresponding 3,4-dihydro-3-$R_1$-4-$R_2$-5-Q-6-R-2(1H)-pyridinones of Examples C-9 through C-17 can be obtained.

C-9. 3,4-Dihydro-3,4,6-trimethyl-5-(4-pyridinyl)-2(1H)-pyridinone, using 4-acetyl-2,3-dimethyl-4-(4-pyridinyl)butanenitrile or ethyl 4-acetyl-2,3-dimethyl-4-(pyridinyl)butanoate.

C-10. 3,4-Dihydro-6-methyl-5-(3-pyridinyl)-2(1H)-pyridinone, using 4-acetyl-4-(3-pyridinyl)butanenitrile or ethyl 4-acetyl-4-(3-pyridinyl)butanoate.

C-11. 6-Ethyl-3,4-dihydro-3-methyl-5-(4-pyridinyl)-2(1H)-pyridinone, using 2-methyl-4-n-propanoyl-4-(4-pyridinyl)butanenitrile or ethyl 2-methyl-4-n-propanoyl-4-(4-pyridinyl)butanoate.

C-12. 3,4-Dihydro-6-isopropyl-3-methyl-5-(4-pyridinyl)-2(1H)-pyridinone, using 2-methyl-4-(3-methyl-n-propanoyl)-4-(4-pyridinyl)butanenitrile or ethyl 2-methyl-4-(3-methyl-n-propanoyl)-4-(4-pyridinyl)butanoate.

C-13. 6-n-Butyl-3,4-dihydro-3-methyl-5-(4-pyridinyl)-2(1H)-pyridinone, using 2-methyl-4-(n-pentanoyl)-4-(4-pyridinyl)butanenitrile or ethyl 2-methyl-4-(n-pentanoyl)-4-(4-pyridinyl)butanoate.

C-14. 3,4-Dihydro-3,4,6-trimethyl-5-(2-methyl-4-pyridinyl)-2(1H)-pyridinone, using 4-acetyl-2,3-dimethyl-4-(2-methyl-4-pyridinyl)butanitrile or ethyl 4-acetyl-2,3-dimethyl-4-(2-methyl-4-pyridinyl)butanoate.

C-15. 6-Ethyl-3,4-dihydro-3-methyl-5-(2,6-dimethyl-4-pyridinyl)-2(1H)-pyridinone, using 2-methyl-4-(2,6-dimethyl-4-pyridinyl)-4-n-propanoylbutanenitrile or ethyl 2-methyl-4-(2,6-dimethyl-4-pyridinyl)-4-n-propanoylbutanoate.

C-16. 3,4-Dihydro-5-(4-methoxyphenyl)-3,6-dimethyl-2(1H)-pyridinone, using 4-acetyl-4-(4-methoxyphenyl)-2-methylbutanenitrile or ethyl 4-acetyl-4-(4-methoxyphenyl)-2-methylbutanoate.

C-17. 6-Ethyl-3,4-dihydro-5-(3-methoxhphenyl)-3-methyl-2(1H)-pyridinone, using 4-(3-methoxyphenyl)-2-methyl-4-n-propanoylbutanenitrile or ethyl 4-(3-methoxyphenyl)-2-methyl-4-n-propanoylbutanoate.

C-18. 6-Ethyl-3,4-dihydro-5-(3-hydroxyphenyl)-3-methyl-2(1H)-pyridinone can be prepared following the procedure described in Example C-6 using in place of 3,4-dihydro-5-(4-methoxyphenyl)-3,6-dimethyl-2(1H)-pyridinone a molar equivalent quantity of the corresponding 3,4-dihydro-5-(3-methoxyphenyl)-3,6-dimethyl-2(1H)-pyridinone.

Following the procedure described in Example C-4 but using in place of 1-(4-pyridinyl)-2-propanone and α-methylacrylamide corresponding molar equivalent quantities of the respective 1-Q-2-alkanone and α-$R_1$-β-$R_2$-acrylamide, it is contemplated that the corresponding 3,4-dihydro-3-$R_1$-4-$R_2$-5-Q-6-R-2(1H)-pyridinones of Examples C-19 through C-23 can be obtained.

C-19. 3,4-Dihydro-3,4,6-trimethyl-5-(4-pyridinyl)-2(1H)-pyridinone, using 1-(4-pyridinyl)-2-propanone and α-β-dimethylacrylamide.

C-20. 3,4-Dihydro-3,6-dimethyl-5-(3-pyridinyl)-2(1H)-pyridinone, using 1-(3-pyridinyl)-2-propanone and α-methylacrylamide.

C-21. 3,4-Dihydro-3,6-dimethyl-5-(2-methyl-4-(pyridinyl)-2(1H)-pyridinone, using 1-(2-methyl-4-pyridinyl)-2-propanone and α-methylacrylamide.

C-22. 3,4-Dihydro-3,6-dimethyl-5-(2,6-dimethyl-4-pyridinyl)-2(1H)-pyridinone, using 1-(2,6-dimethyl-4-pyridinyl)-2-propanone and α-methylacrylamide.

C-23. 6-Ethyl-3,4-dihydro-3-methyl-5-(4-pyridinyl)-2(1H)-pyridinone, using 1-(4-pyridinyl)-2-butanone and α-methylacrylamide.

The utility of the compounds of formula I where Q is 4(or 3)-hydroxyphenyl, 4(or 3)-pyridinyl or 4(or 3)-pyridinyl having one or two lower-alkyl substituents (or pharmaceutically acceptable acid-addition salts when Q is a pyridinyl substituent) as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat or guinea pig atria and papillary muscle procedure, the compounds of the invention or said salts thereof at doses of 1, 3, 10, 30, and/or 100 μg/ml., were found to cause significant increases, that is, greater than 25% (cat) or 30% (g. pig) in papillary muscle force and significant increases, that is greater than 25% (cat) or 30% (g. pig) in right atrial force, while causing a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, illustrative cat papillary muscle and right atrial force increases for a compound of the invention are: 175% and 64% at 100 μg/ml, 129% and 53% at 30 μg/ml, and 109% and 51% at 10 μg/ml for the compound of Example C-2. Further, illustrative guinea pig papillary muscle and right atrial force increases for other compounds of the invention are: 100% and 118% at 100 μg/ml, 131% and 98% at 30 μg/ml and 110% and 64% at 10 μg/ml for the compound of Example C-1; 157% and 161% at 10 μg/ml, 127% and 73% at 3 μg/ml and 52% and 39% at 1 μg/ml for the compound of Example C-4; 104% and 87% at 10 μg/ml, and 64% and 72% at 3 μg/ml for the compound of Example C-6; and, 104% and 132% at 10 μg/ml for the compound of Example C-8.

When tested by said anesthetized dog procedure, the compounds of the invention or said salts thereof at doses of 0.10, 0.30, 1.0 and/or 3.0 mg/kg administered intravenously were found to cause significant increases, that is, 25% or greater, in cardiac contractile force or cardiac contractility with lower changes in heart rate and blood pressure. For example, the compound of Example C-4 was found to cause respective increases of 51% and 87% in contractile force (cf) at doses of 0.10 and 0.30 mg/kg; and, the compound of Example C-6 was found to cause respective cf increases of 41%, 77% and 107% at doses of 0.3, 1.0 and 3.0 mg/kg.

The present invention includes within its scope a cardiotonic composition for increasing cardiac contractility, said composition comprising a pharmaceutically acceptable carrier and, as the active component thereof, a cardiotonically effective amount of the compound of formula I where Q is 4(or 3)-hydroxyphenyl, 4(or 3)-pyridinyl or 4(or 3)-pyridinyl having one or two lower-alkyl substituents or said salt thereof. The invention also includes within its scope the method for increasing cardiac contractility in a patient requiring such treatment which comprises administering to such patient said cardiotonic composition providing a cardiotonically effective amount of the said compound of formula I or said salt thereof. In clinical practice said compound will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin.

Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. 3,4-Dihydro-3-$R_1$-4-$R_2$-5-Q-6-R-2(1H)-pyridinone having the formula

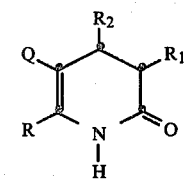

where Q is 4(or 3)-hydroxyphenyl, 4(or 3)-methoxyphenyl, 4(or 3)-pyridinyl or 4(or 3)-pyridinyl having one or two lower-alkyl substituents, $R_1$ and $R_2$ are each hydrogen or methyl and R is lower-alkyl, or an acid-addition salt thereof when Q is a pyridinyl substituent.

2. A compound according to claim 1 where Q is 4(or 3)-pyridinyl, R is methyl or ethyl and at least one of $R_1$ or $R_2$ is methyl.

3. 3,4-Dihydro-6-methyl-5-(4-pyridinyl)-2(1H)-pyridinone according to claim 1 or acid-addition salt thereof.

4. 3,4-Dihydro-4,6-dimethyl-5-(4-pyridinyl)-2(1H)-pyridinone according to claim 1 or acid-addition salt thereof.

5. 3,4-Dihydro-3,6-dimethyl-5-(4-pyridinyl)-2(1H)-pyridinone according to claim 1 or acid-addition salt thereof.

6. 3,4-Dihydro-5-(4-hydroxyphenyl)-6-methyl-2(1H)-pyridinone according to claim 1.

7. 3,4-Dihydro-5-(4-hydroxyphenyl)-3,6-dimethyl-2(1H)-pyridinone according to claim 1.

8. A cardiotonic composition for increasing cardiac contractility, said composition comprising a pharmaceutically acceptable carrier and, as the active component thereof, a cardiotonically effective amount of the compound having the formula

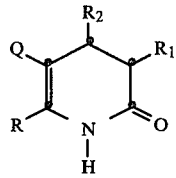

where R is lower-alkyl, $R_1$ and $R_2$ are each hydrogen or methyl and Q is 4(or 3)-hydroxyphenyl, 4(or 3)-pyridinyl or 4(or 3)-pyridinyl having one or two lower alkyl substituents, or pharmaceutically acceptable acid-addition salt thereof when Q is a pyridinyl substituent.

9. A composition according to claim 8 where the active component is the compound where Q is 4(or 3)-pyridinyl, R is methyl or ethyl and at least one of $R_1$ or $R_2$ is methyl.

10. The method for increasing cardiac contractility in a patient requiring such treatment which comprises administering orally or parenterally in a solid or liquid dosage form to such patient a composition according to claim 8.

11. The method for increasing cardiac contractility in a patient requiring such treatment which comprises administering orally or parenterally in a solid or liquid dosage form to such patient a composition according to claim 8 where Q is 4(or 3)-pyridinyl, R is methyl or ethyl and at least one of $R_1$ or $R_2$ is methyl.

12. The process for preparing 3,4-dihydro-3-$R_1$-4-$R_2$-5-Q-6-R-2(1H)-pyridinone of the formula

which comprises reacting a 1-Q-2-alkanone of the formula Q—$CH_2$—C(=O)R with an α-$R_1$-β-$R_2$-acrylonitrile of the formula $R_2$—CH=C($R_1$)CN in the presence of a strong base to produce 2-$R_1$-3-$R_2$-4-Q-4-(RCO)-butanenitrile of the formula

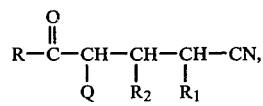

reacting 2-$R_1$-3-$R_2$-4-Q-4(RCO) butanenitrile with a strong acid to produce said 3,4-dihydro-3-$R_1$-4-$R_2$-5-Q-6-R-2(1H)-pyridin-one of the formula given above, where $R_1$ and $R_2$ are each hydrogen or methyl, R is lower-alkyl, and Q is 4(or 3)-methoxyphenyl, 4(or 3)-pyridinyl or 4(or 3)-pyridinyl having one or two lower-alkyl substituents, and converting said 3,4-dihydro-3-$R_1$-4-$R_2$-5-Q-6-R-2(1H)-pyridinone where Q is 4(or 3)-methoxyphenyl to the corresponding compound where Q is 4(or 3)-hydroxyphenyl.

13. The process according to claim 12 where the strong base in the first step is an alkali hydride or methoxide, the strong acid in the second step is a strong mineral acid and the products produced thereby are those where Q is 4(or 3)-pyridinyl, R is methyl or ethyl and at least one of $R_1$ or $R_2$ is methyl.

14. The process for preparing 3,4-dihydro-3-$R_1$-4-$R_2$-5-Q-6-R-2(1H)-pyridinone having the formula

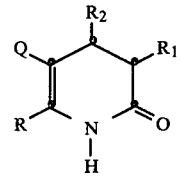

which comprises reacting a 1-Q-2-alkanone of the formula Q—$CH_2$—C(=O)R with a lower-alkyl α-$R_1$-β-$R_2$-acrylate of the formula $R_2$—CH=CH($R_1$)COO$R_3$ to produce lower-alkyl 2-$R_1$-3-$R_2$-4-Q-4-(RCO)butanoate having the formula

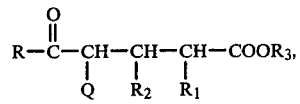

reacting said lower-alkyl 2-$R_1$-3-$R_2$-4-Q-4-(RCO)-butanoate with ammonia or source thereof to produce said 3,4-dihydro-4-$R_2$-5-Q-6-R-2(1H)-pyridinone, where $R_1$ and $R_2$ are each hydrogen or methyl, R is lower-alkyl, and Q is 4(or 3)-methoxyphenyl, 4(or 3)-pyridinyl or 4(or 3)-pyridinyl having one or two lower-alkyl substituents, and converting said 3,4-dihydro-3-$R_1$-4-$R_2$-5-Q-6-R-2(1H)-pyridinone where Q is 4(or 3)-methoxyphenyl to the corresponding compound where Q is 4(or 3)-hydroxyphenyl.

15. The process according to claim 14 where $R_3$ in the first step is methyl or ethyl, ammonium acetate is used as the source of ammonia in the second step and the products produced are those where Q is 4(or 3)-pyridinyl, R is methyl or ethyl and at least one of $R_1$ or $R_2$ is methyl.

16. The process for preparing 3,4-dihydro-3-$R_1$-4-$R_2$-5-Q-6-R-2(1H)-pyridinone having the formula

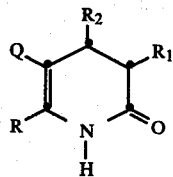

which comprises reacting an α-$R_1$-β-$R_2$-acrylamide of the formula $R_2$—CH=C($R_1$)CONH$_2$ in an inert solvent in the presence of a strong base to produce said 3,4-dihydro-3-$R_1$-4-$R_2$-5-Q-6-R-2(1H)-pyridinone, where $R_1$ and $R_2$ are each hydrogen or methyl, R is lower-alkyl and Q is 4(or 3)-methoxyphenyl, 4(or 3)-pyridinyl or 4(or 3)-pyridinyl having one or two lower-alkyl substituents, and converting said 3,4-dihydro-3-$R_1$-4-$R_2$-5-Q-6-R-2(1H)-pyridinone where Q is 4(or 3)-methoxyphenyl to the corresponding compound where Q is 4(or 3)-hydroxyphenyl.

17. The process according to claim 16 where dioxane and potassium or sodium tertiary-butoxide are used in the first step and the products produced are those where Q is 4(or 3)-pyridinyl, R is methyl or ethyl and at least one of $R_1$ or $R_2$ is methyl.

* * * * *

UNITED STATES PATENT AND TRADEMARK OFFICE
CERTIFICATE OF CORRECTION

PATENT NO. : 4,431,651

DATED : February 14, 1984

INVENTOR(S) : G.Y. Lesher et al.

It is certified that error appears in the above-identified patent and that said Letters Patent is hereby corrected as shown below:

Column 6, lines 4-5, "temperature alternatively" should read -- temperature. Alternatively --.

Column 16, line 8, "2-$R_1$-3-$R_2$-4-Q-4(RCO) butanenitrile" should read -- 2-$R_1$-3-$R_2$-4-Q-4-(RCO)butanenitrile --.

Column 17, line 10, between "reacting" and "an" insert -- a 1-Q-2-alkanone of the formula Q-$CH_2$-C(=O)R with --.

Signed and Sealed this

Seventeenth Day of September 1985

[SEAL]

Attest:

DONALD J. QUIGG

Attesting Officer

Commissioner of Patents and Trademarks—Designate